(12) United States Patent
Unadkat

(10) Patent No.: US 6,251,584 B1
(45) Date of Patent: Jun. 26, 2001

(54) SPECIFIC BINDING ASSAYS USING METHYL ORANGE

(75) Inventor: Pratul Unadkat, Serangoon Central (SG)

(73) Assignee: Ortho-Clinical Diagnostics, Amersham (GB)

( * ) Notice: Subject to any disclaimer, the term of this patent is extended or adjusted under 35 U.S.C. 154(b) by 0 days.

(21) Appl. No.: 09/327,809

(22) Filed: Jun. 8, 1999

(30) Foreign Application Priority Data

Jun. 22, 1998 (GB) .................................................. 9813450

(51) Int. Cl.$^7$ ............................. C12Q 1/70; G01N 33/53; G01N 33/566; G01N 33/532
(52) U.S. Cl. ................................ 435/5; 435/7.1; 435/7.9; 435/7.92; 435/960; 436/518; 436/544; 436/820
(58) Field of Search .............................. 436/518, 10, 501, 436/570, 544, 820; 435/5, 6, 7, 7.1, 7.9, 7.92, 960; 530/350, 403, 810, 826

(56) References Cited

U.S. PATENT DOCUMENTS

| | | | |
|---|---|---|---|
| 5,447,838 | * 9/1995 | Meiklejohn et al. | 435/5 |
| 5,683,864 | * 11/1997 | Houghton et al. | 435/5 |
| 5,705,330 | 1/1998 | Shah et al. . | |

FOREIGN PATENT DOCUMENTS

| | | |
|---|---|---|
| 0 785 431 A1 | 7/1997 | (EP) . |
| WO 89/00292 | 1/1989 | (WO) . |

OTHER PUBLICATIONS van der Poel, Cees L., et al., "Hepatitis C virus six years on", *The Lancet*, vol. 344, Nov. 26, 1994 pp. 1475–1479.

Uyttendaele, S., et al., "Evaluation of the Third–Generation Screening and Confirmatory Assays for HCV Antibodies", *Vox Sang* 1994;66:122–1290.

* cited by examiner

*Primary Examiner*—Donna C. Wortman
*Assistant Examiner*—Robert A. Zeman
(74) *Attorney, Agent, or Firm*—Stacy B. Antar

(57) ABSTRACT

The present invention relates to a method for improving the specificity of a specific binding assay by adding methyl orange to a coating solution in an amount sufficient for improving specificity of an immunoassay conducted using said coating. The present invention also relates to a method for the detection of antibodies to hepatitis C virus is performed by, i) providing a solid phase comprising a coating solution comprising methyl orange and at least one first binding ligand for antibodies to hepatitis C virus; ii) contacting the solid phase with a sample that may contain antibodies to hepatitis C virus; iii) contacting the solid phase with at least one second binding ligand for antibodies to hepatitis C virus, said second ligand labelled directly or indirectly with a detectable group and iv) measuring the amount of the detectable group bound to the solid phase.

6 Claims, 2 Drawing Sheets

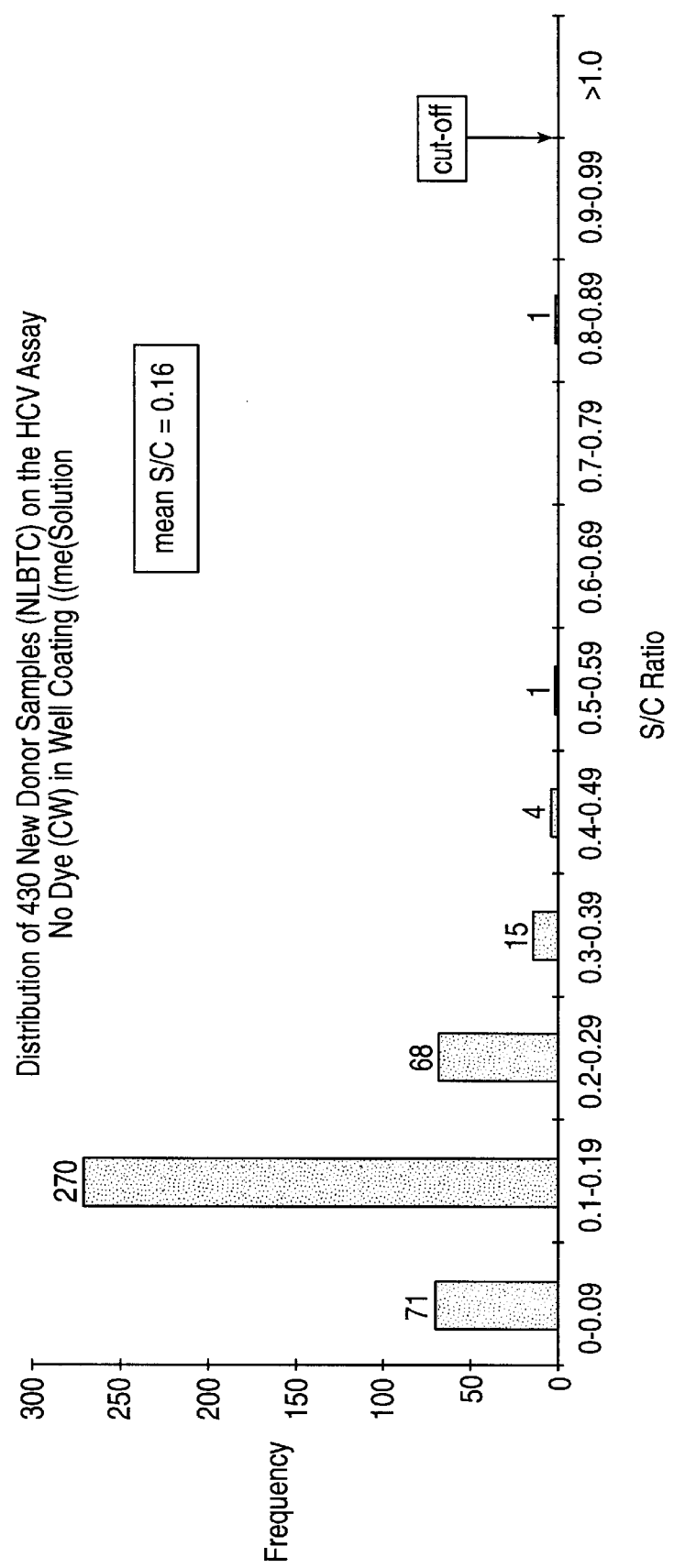

SPECIFIC BINDING ASSAYS USING METHYL ORANGE

BACKGROUND OF THE INVENTION

Specific binding assays, for example immunoassays, which take advantage of natural binding reactions, have found wide-spread use as analytical techniques in clinical chemistry. Because of the specificity of the reactions, they are particularly advantageous in quantifying biological analytes that are present in very low concentration in biological fluids. Such analytes include, for example, antigens, antibodies, therapeutic drugs, narcotics, enzymes, hormones, proteins, etc.

Many dyes or colorants (hereinafter "dyes") are used in commercial immunoassay coating procedures to aid monitoring of the dispensing of a reagent or spectrophotometric monitoring of the dispensing of reagent. Many of the dyes are commercially available. Basically, the dye allows for visual detection. This can be particularly useful in monitoring the dispensing of solutions into vessels, e.g., microwells during manufacturing processes for coating biological materials onto the surface of the microwells. The coated vessels are subsequently used as solid phase in immunoassays. It is desirable that the dyes that are used do not interfere with the biological nature of proteins, which are coated onto the solid phase support. However, some proteins can interact with dyes and, as a result, this interaction reduces assay performance. For example, this has been a recognized problem in the manufacturing of microwells for assays for detecting antibodies to hepatitis C virus (HCV).

Therefore, one object of the present invention is to provide a dye that can be used in a solid phase coating comprising HCV antigens and to aid the monitoring of microwell fill volume and yet, does not have a detrimental effect on proteins, specifically HCV antigens, present in an anti-HCV assay. Another object of the present invention is to provide a dye that will actually improve assay performance.

SUMMARY OF THE INVENTION

The invention relates to adding dyes, particularly methyl orange, to a coating solution used in a procedure to prepare a solid phase for use in a specific binding assay and for monitoring the volume of coating solution dispensed into a vessel. Many dyes were investigated for use in anti-hepatitis C virus immunoassay coating formulations to enable a colorimetric monitoring and process control of coating volumes dispensed in the solid phase. Many of the dyes reduced the activity of the HCV recombinant coating proteins. Unexpectedly the applicant found that upon the addition of methyl orange not only could volumes of coating solution be monitored, but also, the use of methyl orange as a dye positively interacts with proteins, especially HCV antigens, resulting in improved specificity of results in an assay. Therefore, as shown by the comparison of FIGS. 1a and 1b, a solution for coating a solid phase comprising methyl orange allows for greater discrimination of negative samples from positive samples.

Therefore one embodiment of the present invention provides a solid phase to be used for a specific binding assay comprising at least one immobilized HCV antigen that has been treated with methyl orange. A preferred embodiment of the invention is where the HCV antigen is expressed from the NS3 and/or NS4 regions of the viral genome. A more preferred embodiment is where the HCV antigen is c200.

It is a further object of the present invention to provide a method for improving the specificity of an anti-HCV immunoassay by adding methyl orange to a coating solution in an amount sufficient for improving specificity of an immunoassay conducted using said coating.

In a preferred embodiment of this aspect of the invention, a method for the detection of antibodies to hepatitis C virus is performed by, i) providing a solid phase comprising a coating solution comprising methyl orange and at least one first binding ligand for antibodies to hepatitis C virus; ii) contacting the solid phase with a sample that may contain antibodies to hepatitis C virus; iii) contacting the solid phase with at least one second binding ligand for antibodies to hepatitis C virus, said second ligand labelled directly or indirectly with a detectable group and iv) measuring the amount of the detectable group bound to the solid phase. Alternatively, the amount of detectable group not bound to the solid phase can be measured as an indication of the presence of antibodies to HCV. The detectable group can be, for example, an enzyme, a radioactive atom, a fluorescent molecule or a luminescent molecule.

A preferred detectable group is an enzyme. The assay can be carried out using any enzyme label, which can be attached to the ligand to form a labelled ligand. Enzymes such as oxidases, e.g., glucose oxidase, peroxidases, e.g., horseradish peroxidase (HRP), alkaline phosphatase and galactosidases are preferred labels. It is within the skill of the ordinary worker in clinical chemistry to determine a suitable substrate for a given label. The substrate can be a material that is directly acted upon by the enzyme label or a material that is involved in a series of reactions, which involve enzymatic reaction of the label.

It will be understood by one of ordinary skill in the art that steps i) through iv) above can be done sequentially or simultaneously. It will also be understood that the first and second binding ligands can be the same or different from themselves or each other. Furthermore, the amount of detectable group measured can be correlated to the amount of anti-HCV present in the sample.

Finally, another embodiment of the present invention provides a method for coating a solid phase for an immunoassay, the improvement comprising: adding methyl orange to a coating solution in an amount sufficient for improving specificity of the immunoassay.

Other advantages of the present invention will become clear from the following more detailed description and the following examples.

BRIEF DESCRIPTION OF THE DRAWINGS

FIG. 1a represents a histogram of samples without methyl orange in the microwell coating.

DETAILED DESCRIPTION OF THE INVENTION

Figure 1B:
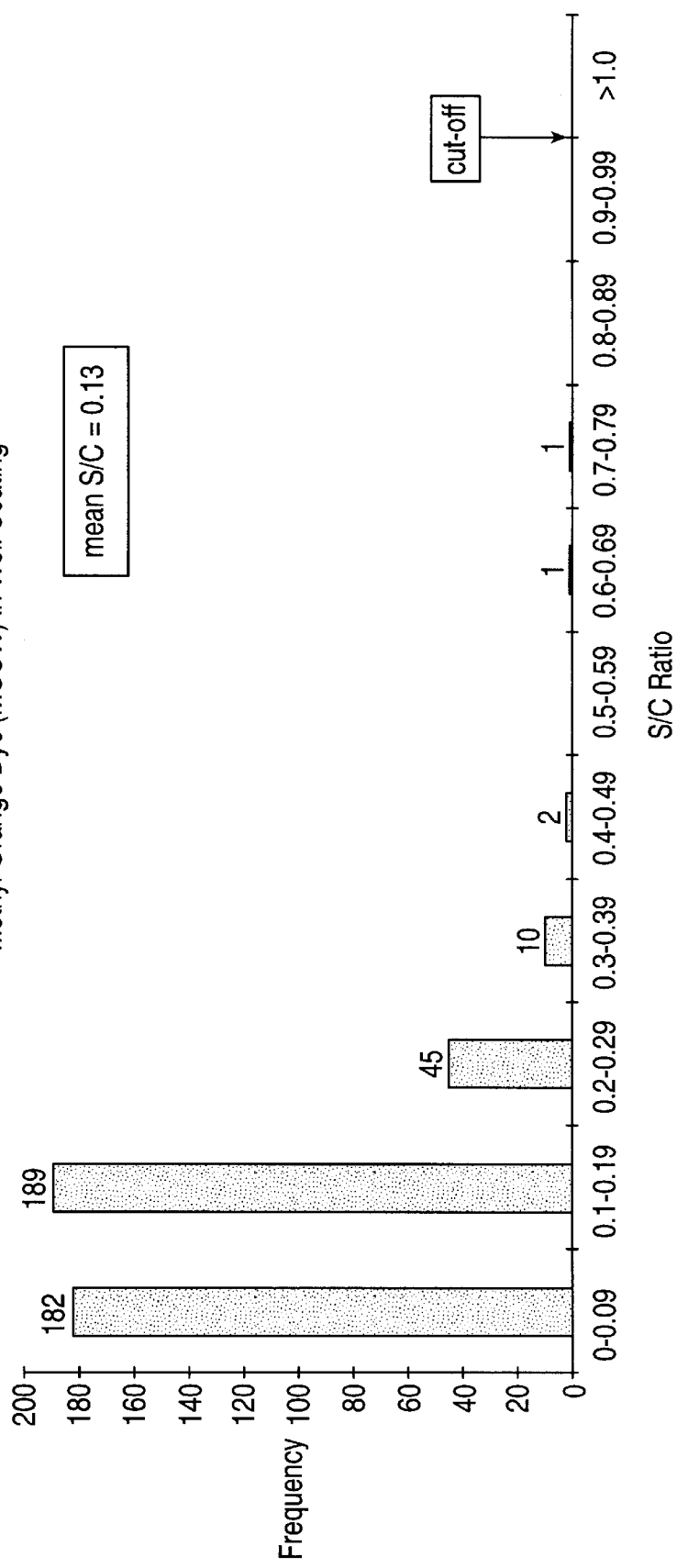
FIG. 1b represents a histogram of samples with methyl orange in the microwell coating.

Methyl orange dye is amphoteric, slightly soluble in water and a mono azo dye (Reagent Chemicals, 7th Ed., Amer. Chem. Society, Washington, D.C., 1986, pp. 434–435). The empirical formula for methyl orange is $(CH_3)_2NC_6H_4N=NC_6H_4SO_3Na$. Its most common applications have been in the textile industry, commonly to dye wool and silk from an acid bath and titrating mineral acids (Analytical Chemistry (II), 9th Ed., John Wiley & Sons, 1942, pp. 467–469), indicating strong bases and estimating alkalinity of waters (Merck Index, 11th Ed, 6019). Biological applications of methyl orange include staining for pituitary acidophils (Kreyberg stain) and plant material (Flemmings stain).

In a "specific binding assay" in which binding partners are utilized, a "binding ligand" can be either component of a pair of binding partners. The most commonly used binding partners are antibodies and antigens or haptens but other binding proteins receptors and biological molecules which can partake in specific binding reactions can be used. For the binding reaction between the antibody and an antigen, either of the antibody or the antigen can be a binding ligand.

A "solid phase" as used herein, refers to any material which is insoluble and to which a binding ligand can be attached directly or indirectly for use in a specific binding assay. The solid phase can be chosen for its intrinsic ability to attract and immobilize a binding ligand. Alternatively the solid phase can retain the ability to immobilize the binding ligand through a specific binding reaction using avidin or streptavidin and biotin. Natural, synthetic, or naturally occurring materials that are synthetically modified can be used as a solid phase. A preferable material for use in a solid phase is polystyrene. Optionally a solid phase can be in the form of particles, dipsticks, or the vessel in which the specific binding assay is performed.

A "coating solution" as used herein, refers to any solution or reagent that is contacted with the solid phase prior to conducting a specific binding assay. The coating may contain, but is not limited to, proteins and/or buffers. One skilled in the art will understand how to make and apply suitable coatings to suitable solid phases.

A "sample" as used herein, refers to any substance that may contain the analyte of interest. A sample can be biological fluid, such as whole blood or whole blood components including red blood cells, white blood cells, platelets, serum and plasma, ascites, urine, cerebrospinal fluid, and other constituents of the body, which may contain the analyte of interest. Optionally, samples may be obtained from water, soil, and vegetation.

HCV antigens expressed from the NS3/NS4 regions, particularly c200 can be prepared for example, using known recombinant DNA techniques. The HCV sequence ("HCV-1") is available from GENBANK, Accession No. M62321 (Nucleic Acid Res., 22:3441–3444 (1994). Also, how to prepare recombinant HCV proteins is described in U.S. Pat. No. 5,705,330.

The HCV genome and deduced recombinant proteins are shown in Vox Sang, 66:122–129 (1994) by Uyttendaele et al. In particular the amino acid sequence for c200 is AA1192–1931. Further discussion of the organization of the HCV genome can be found in The Lancet, 344:1475–1479 (1994) by Cees L. Van der Poel et al.

The present invention uses methyl orange in solid phase coating solutions to allow colorimetric process control and which unexpectedly improves assay performance. The addition of methyl orange in the coating solutions was shown to positively interact with the HCV recombinant proteins to allow colorimetric process control and improve assay specificity.

The effectiveness and advantages of the invention are further illustrated by the following examples. The examples are meant to illustrate, but not to limit, the scope and spirit of the invention.

EXAMPLE 1

Applications of Methyl Orange during HCV Antigen Coating Process

AMERLITE polystyrene microwells (Ortho-Clinical Diagnostics, U.K.) were coated with HCV antigens (c22-3, c200 & NS-5, obtained from Chiron Corporation, Emeryville, Calif., USA), by incubating the microwells with 200 µl of either Coating Buffer 1 or Coating Buffer 2, the formulations of which are given below. The wells were incubated for 16 hours at room temperature. After washing with a TRIS buffer pH 8.5, containing sucrose, saline and Bovine Serum Albumin (BSA), the microwells were dried and stored with desiccant at 2–8° C.

| Coating Buffer 1, pH 6.95–7.05 | |
|---|---|
| Sodium Phosphate Dibasic | 5.45 g/L |
| Potassium Phosphate Monobasic | 1.55 g/L |
| 2-Chloroacetamide | 1.00 g/L |
| EDTA | 0.744 g/L |
| BSA (Protease free) | 0.004 g/L |
| c22-3 | 0.6 mg/L |
| c200 | 1.0 mg/L |
| NS-5 | 0.25 mg/L |
| Deionized water | to 1 L |
| Coating Buffer 2, pH 6.95–7.05 | |
| Methyl Orange in Coating Buffer 1 | 0.003 g/L |

The performance of the coated microwells was assessed using the following assay protocol to measure antibodies to HCV: 20 µl of a sample (pooled human plasma with known anti-HCV activity) and 160 µl sample diluent (phosphate buffered saline, pH 7.4) were added to the HCV coated microwells and the microwells incubated for 30 minutes at 37° C. in an AMERLITE Incubator. After washing the microwells on an AMERLITE Washer, 180 µl horseradish peroxidase (HRP) labeled monoclonal antibody directed against human IgG was added and the microwells incubated for a further 15 minutes. After again washing the microwells on an AMERLITE Washer the HRP activity was measured by an enhanced luminescence reaction [Whitehead et al. (1983), Nature 305, 1158–159]. AMERLITE Signal Reagent, containing luminogenic substrates (a luminol derivative and a peracid salt) and an enhancer (a substituted phenol), was added to the microwells to initiate the light emitting reaction. The light signals were read in an AMERLITE Analyzer.

A cut off value was set at the light signal obtained for a known positive sample (contains anti-HCV activity) in the assay multiplied by a conversion factor, so that for unknown samples a signal to cut off ratio (S/C) value of $\geq 1$ indicates a reactive sample and the possible presence of anti-HCV. A result of <0.9 indicates a non-reactive sample, negative for anti-HCV. A result of $\geq 0.9$ and <1 indicates a gray zone sample.

Microwells prepared using methyl orange dye in the coating solutions (MO wells) gave lower light signals for the controls in the anti-HCV assay compared with microwells prepared using the coating solutions without dye (control wells) (Table 1). The conversion factor for setting the cut off with respect to the positive control was set at 0.25. The performance of the controls with respect to S/C remained relatively unchanged (Table 1), indicating the addition of methyl orange to the coating buffer had no detrimental effect on the sensitivity of the assay, i.e. the ability of the assay to detect a weakly positive sample.

EXAMPLE 2

Specificity Studies

Microwells were coated with HCV antigens as in Example 1. 430 human blood donor sera, presumed negative for antibodies to HCV, were tested using the microwells, following the anti-HCV assay protocol in Example 1. S/C values for the negative sera were generally lower using the MO wells compared to the control wells (mean S/C=0.13 and 0.16 respectively), (FIG. 1). S/C values ≦0.1 were obtained by 42% of donors using MO wells compared with 17% using control wells. These values relate to results obtained for individual donor sera, and so may not be directly comparable to the results for the control of pooled sera in Example 1. The reduced S/C results for the negative samples leads to an improvement in specificity and better discrimination of negative samples to the cut-off. This improved distribution could be used to optimize the sensitivity and the specificity of the assay by positioning the cut-off appropriately. For example, in Example 3 the conversion factor for setting the cut off with respect to the positive control was set at 0.33 to optimize the performance of the assay.

EXAMPLE 3

Sensitivity Studies

Microwells were coated with HCV antigens as in example 1. Commercial seroconversion panels, obtained from Boston Biomedica Inc, West Bridgewater, Mass., USA, were used to assess the clinical sensitivity of the anti- HCV assay, following the assay protocol in Example 1. The S/C ratio was calculated using a cut off value of the positive control signal multiplied by a conversion factor of 0.33. The results for the seroconversion panels in the assays were the same using MO wells and control wells (Tables 2 a–e). There was no change in the negative or positive status of the samples and therefore the addition of methyl orange in the coating formulations had no detrimental effect on the sensitivity of the assay.

TABLE 1

Signal (Light Units) and Assay Result (S/C) of anti-HCV Assay, Using Microwells With Methyl Orange (MO) and Without Methyl Orange (Control) In the Coating Buffer Solutions

|  | Negative Sample | | Weak Positive Sample | | Positive Sample | |
| --- | --- | --- | --- | --- | --- | --- |
|  | Signal | S/C | Signal | S/C | Signal | S/C |
| Control microwells | 37.8 | 0.10 | 689.0 | 1.81 | 1522.5 | 4.0 |
| MO microwells | 22.5 | 0.08 | 615.5 | 2.10 | 1194.0 | 4.0 |

S/C = Sample/[Pos. Control × 0.25]

Seroconversion Studies on Boston Biomedica Inc. Panels in anti-HCV Assay Using Microwells With Methyl Orange (MO) and Without Methyl Orange (Control) In the Coating Buffer Solutions TABLE 2a BBI PHV 906 Panel

|  | Control Microwells | | MO Microwells | |
| --- | --- | --- | --- | --- |
| Sample | Signal | S/C | Signal | S/C |
| PHV906-01 | 1475 | 2.7 | 1602 | 3.1 |
| PHV906-02 | 1599 | 2.9 | 1647 | 3.2 |
| PHV906-03 | 1967 | 3.5 | 2021 | 3.9 |
| PHV906-04 | 2441 | 4.4 | 2340 | 4.5 |
| PHV906-05 | 2760 | 5.0 | 2845 | 5.5 |
| PHV906-06 | 3014 | 5.4 | 3182 | 6.1 |
| PHV906-07 | 3170 | 5.7 | 3394 | 6.5 |

S/C = Sample/[Pos. Ctrl × 0.33]

TABLE 2b

BCP 6211 Panel

|  | Control Microwells | | MO Microwells | |
| --- | --- | --- | --- | --- |
| Sample | Signal | S/C | Signal | S/C |
| 6211-37 | 56 | 0.1 | 67 | 0.1 |
| 6211-38 | 897 | 1.7 | 821 | 1.7 |
| 6211-39 | 1875 | 3.5 | 1729 | 3.6 |
| 6211-40 | 2334 | 4.3 | 2219 | 4.6 |

S/C = Sample/[Pos. Ctrl × 0.33]

TABLE 2c

BCP 6212 Panel

|  | Control Wells | | MO Wells | |
| --- | --- | --- | --- | --- |
| Sample | Signal | S/C | Signal | S/C |
| 6212-1 | 21.5 | 0.0 | 41.6 | 0.1 |
| 6212-2 | 618 | 1.1 | 611 | 1.3 |
| 6212-3 | 662 | 1.2 | 610 | 1.3 |
| 6212-4 | 1524 | 2.8 | 1505 | 3.1 |
| 6212-5 | 1785 | 3.3 | 1693 | 3.5 |
| 6212-6 | 1960 | 3.6 | 1786 | 3.7 |
| 6212-7 | 1921 | 3.6 | 1761 | 3.6 |
| 6212-8 | 3440 | 6.4 | 3202 | 6.6 |
| 6212-9 | 3524 | 6.5 | 3369 | 6.9 |

S/C = Sample/[Pos. Ctrl × 0.33]

TABLE 2d

BCP 6213 Panel

|  | Control Wells | | MO Wells | |
| --- | --- | --- | --- | --- |
| Sample | Signal | S/C | Signal | S/C |
| 6213-1 | 119 | 0.2 | 126 | 0.2 |
| 6213-2 | 115 | 0.2 | 135 | 0.3 |
| 6213-3 | 114 | 0.2 | 120 | 0.2 |
| 6213-4 | 117 | 0.2 | 124 | 0.2 |
| 6213-5 | 116 | 0.2 | 122 | 0.2 |
| 6213-6 | 132 | 0.2 | 157 | 0.3 |
| 6213-7 | 119 | 0.2 | 119 | 0.2 |
| 6213-8 | 102 | 0.2 | 114 | 0.2 |
| 6213-9 | 131 | 0.2 | 144 | 0.3 |
| 6213-10 | 807 | 1.5 | 777 | 1.5 |
| 6213-11 | 4083 | 7.4 | 4180 | 8.0 |
| 6213-12 | 4190 | 7.6 | 4527 | 8.7 |

S/C = Sample/[Pos. Ctrl × 0.33]

TABLE 2e

BBI PHV 903 Panel

|  | Control Wells | | MO Wells | |
| --- | --- | --- | --- | --- |
| Sample | Signal | S/C | Signal | S/C |
| PHV903-01 | 115.4 | 0.21 | 111.6 | 0.21 |
| PHV903-02 | 287.9 | 0.52 | 260.5 | 0.50 |
| PHV903-03 | 557.4 | 1.00 | 533.3 | 1.03 |
| PHV903-04 | 930.7 | 1.68 | 936.0 | 1.80 |
| PHV903-05 | 1057.6 | 1.91 | 1081.2 | 2.08 |
| PHV903-06 | 2515.2 | 4.53 | 2615.4 | 5.03 |
| PHV903-07 | 3064.2 | 5.52 | 3323.3 | 6.39 |
| PHV903-08 | 3504.0 | 6.31 | 3741.2 | 7.20 |

S/C = Sample/[Pos. Ctrl × 0.33]

It would be understood by one skilled in the art that the concentration of the dye could be monitored spectrophotometrically at 450 nm and thus can be used as an aid inprocess control for the copating of wells by enabling the measurement of the volume of the coating solution dispensed into optically clear microwells at intervals during the dispensing procedure. All materials cited herein are hereby incorporated by reference. Accordingly it should be understood that the present invention includes all modifications falling within the scope of the following claims.

We claim:

1. A method for improving the specificity of an anti-hepatitis C virus immunoassay, wherein the improvement comprises exposing an HCV antigen to methyl orange, coupling the HCV antigen to a solid phase and then performing the immunoassay using the solid phase.

2. A method for the detection of antibodies to hepatitis C virus, comprising:

i) providing a solid phase comprising a coating solution comprising methyl orange and at least one first binding ligand for antibodies to hepatitis C virus;

ii) contacting the solid phase with a sample that may contain antibodies to hepatitis C virus;

iii) contacting the solid phase with at least one second binding ligand for antibodies to hepatitis C virus, said second ligand labelled with a detectable group and iv) measuring the amount of the detectable group bound to the solid phase or not bound to the solid phase, as an indication of the presence of antibodies to hepatitis C virus.

3. The method of claim 2 wherein the detectable group is selected from the group consisting of: an enzyme, a radioactive atom, a fluorescent molecule, and a luminescent molecule.

4. The method of claim 2 wherein the first binding ligand is selected from the group consisting of: c200, c22-3, and NS5.

5. The method of claim 4 wherein the second binding ligand is an antibody to human IgG.

6. The method of claim 2 wherein the second binding ligand is an antibody to human IgG.

* * * * *